United States Patent
Siljamaki et al.

(10) Patent No.: US 8,483,357 B2
(45) Date of Patent: Jul. 9, 2013

(54) DOSE CALCULATION METHOD FOR MULTIPLE FIELDS

(75) Inventors: Sami Pekka Siljamaki, Helsinki (FI); Janne Ilmari Nord, Espoo (FI); Laura Kristiina Korhonen, Espoo (FI)

(73) Assignee: Varian Medical Systems International AG, Zug (CH)

( * ) Notice: Subject to any disclaimer, the term of this patent is extended or adjusted under 35 U.S.C. 154(b) by 115 days.

(21) Appl. No.: 13/220,622

(22) Filed: Aug. 29, 2011

(65) Prior Publication Data

US 2012/0051516 A1    Mar. 1, 2012

Related U.S. Application Data

(63) Continuation of application No. 12/582,332, filed on Oct. 20, 2009, now Pat. No. 8,009,804.

(51) Int. Cl.
*A61N 5/10* (2006.01)

(52) U.S. Cl.
USPC .......................................................... 378/65

(58) Field of Classification Search
USPC ................. 378/62, 64, 65, 97, 96, 108, 162, 378/165
See application file for complete search history.

(56) References Cited

U.S. PATENT DOCUMENTS

| | | | |
|---|---|---|---|
| 6,560,312 B2 * | 5/2003 | Cash | 378/65 |
| 7,519,150 B2 * | 4/2009 | Romesberg et al. | 378/65 |
| 7,593,505 B2 * | 9/2009 | Saracen et al. | 378/65 |
| 2006/0067469 A1 * | 3/2006 | Dooley et al. | 378/65 |
| 2010/0054410 A1 * | 3/2010 | Nord et al. | 378/65 |
| 2010/0104068 A1 * | 4/2010 | Kilby et al. | 378/65 |

* cited by examiner

*Primary Examiner* — Irakli Kiknadze
(74) *Attorney, Agent, or Firm* — Kilpatrick Townsend & Stockton LLP (57) ABSTRACT

Systems and methods for developing a treatment plan for irradiating a treatment volume within a patient are disclosed. In accordance with the present invention, control points used to calculate a dose of radiation delivered to the treatment volume may be combined to result in a smaller number of control points. The smaller number of control points may allow more efficient calculation of dose distributions resulting in a treatment plan that can be delivered to the patient earlier or may allow additional iterations of treatment plan optimization resulting in a more accurate dose distribution being delivered to the patient.

20 Claims, 9 Drawing Sheets

DOSE CALCULATION METHOD FOR MULTIPLE FIELDS

CROSS-REFERENCE TO RELATED APPLICATION

This application is a continuation of U.S. application Ser. No. 12/582,332, entitled "Dose Calculation Method for Multiple Fields," filed on Oct. 20, 2009, to issue as U.S. Pat. No. 8,009,804 on Aug. 30, 2011, which is herein incorporated by reference in its entirety for all purposes.

The present invention relates generally to treatment planning for radiation therapy and is more particularly directed to methods of calculating and optimizing a treatment plan.

BACKGROUND OF THE INVENTION

In general, radiation therapy consists of the use of ionizing radiation to treat living tissue, usually tumors. There are many different types of ionizing radiation used in radiation therapy, including high energy x-rays, electron beams, and proton beams. However, the process of administering the radiation to a patient can be somewhat generalized regardless of the type of radiation used.

Modern radiation therapy techniques include the use of Intensity Modulated Radiotherapy ("IMRT"), typically by use of a radiotherapy system, such as a linear accelerator, equipped with a multileaf collimator ("MLC"). Use of multileaf collimators in general, and IMRT in particular, allows the radiologist to treat a patient from multiple angles while varying the shape and dose of the radiation beam, thereby providing greatly enhanced ability to deliver radiation to a target within a treatment volume while avoiding excess irradiation of nearby healthy tissue. However, the greater freedom which IMRT and other complex radiotherapy techniques, such as volumetric modulated arc therapy (where the system gantry moves while radiation is delivered) and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays), particles (such as electron and proton beams), and radiosurgical techniques. While modern linear accelerators use MLCs, other methods of providing conformal radiation to a target volume are known and are within the scope of the present invention.

Treatment planning starts typically with (1) images of the treatment volume (e.g., slices from CT or MRI scans) and, (2) the desired dose of radiation which is to be delivered to a target, such as a tumor, within the treatment volume, and (3) the maximum dose which can be safely absorbed by tissue structures, such as organs, within the treatment volume that are adjacent to or near the tumor or other target volume. As used herein, the term "treatment volume" is used to refer to the entire volume that will be subjected to radiation, and is sometimes referred to as the "irradiated volume." The target volume, intended to receive a therapeutic prescribed dose, is sometimes referred to as the "planning target volume" ("PTV"). Both the target within the treatment volume and any nearby organs may have complex three dimensional shapes adding to the difficulty of preparing a treatment plan.

A variety of algorithms have been developed to solve the "inverse problem" of devising and optimizing a specific, three-dimensional treatment plan for irradiating the treatment volume from a variety of angles or, in arc therapy, while the system gantry is moving, to deliver a desired radiation dose to the target while minimizing irradiation of nearby tissue, taking into account the capabilities and physical limitations of the radiotherapy system. Generally speaking, the inverse problem involves optimizing the angles, MLC leaf movements and durations of irradiations. Because of the large number of variables involved and complex calculation operations that are required, the algorithms for calculating and optimizing treatment plans require substantial computational time even when using modern high speed computers.

Generally two types of algorithms are used in treatment planning: (1) dose calculations algorithms based on a given set system parameters, e.g., gantry angle, MLC leaf positions, etc., and (2) search algorithms which use various techniques to adjust system parameters between dose calculations to achieve optimization of the plan. Some exemplary dose calculation algorithms include various Monte Carlo ("MC") techniques and pencil beam convolution ("PBC"). Some exemplary search algorithms include various stochastic and deterministic methods, including various simulated annealing ("SA") techniques, algebraic inverse treatment planning ("AITP"), and simultaneous iterative inverse treatment planning ("SIITP"). Such techniques, and others, are well known in the art, and each of the techniques has advantages and disadvantages relative to the others. Each of the methods requires iterative dose calculations for optimization, and generally a high number of dose calculation iterations or "passes" are required to converge on an optimal plan. Typically, each iteration involves changing the parameter values using the search algorithm and recalculating the dose distribution. While a fully optimized plan might be achieved using known methods if adequate time is available, as a practical matter time constraints often limit the ability to achieve this goal.

It is noted that a treatment plan is typically implemented over a time period. Thus, the patient typically is given multiple treatments over the course of days or weeks, such that the dose delivered to the treatment volume is fractionated. During the time between treatments changes may occur in the treatment volume, for example, the tumor being irradiated may shrink in size or surrounding organs may change position. Any such changes may necessitate revising and re-optimizing the treatment plan before the next fractional dose is delivered. The problem of re-optimizing a treatment plan is known and will not be discussed further, other than to note that the present invention is equally applicable to re-optimizing the treatment plan.

Treatment planning algorithms may be implemented as part of an overall, integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters. The Eclipse™ Treatment Planning System offered by Varian Medical Systems, Inc. is such an integrated software program.

The substantial computational resources required to develop an acceptable treatment plan within a reasonable period of time presents many challenges. One of these challenges is to develop systems and methods for calculating dose distributions within a treatment volume in a more efficient manner, such that use of the computational resources and finite available time is maximized. Accordingly, there is a need for improved systems and methods to efficiently perform dose distribution calculations to optimize a radiotherapy treatment plan.

BRIEF SUMMARY OF THE INVENTION

The present invention is directed to a method and system for optimizing a treatment plan for irradiating a treatment volume which includes a target volume. In accordance with the present invention, radiation fields produced by multiple control points are reduced into an effective field produced by a fewer number of control points. Specifically, the method and system of some embodiments of the present invention select control points from treatment directions that have smaller impacts on the overall dose distribution and consolidate those control points into a lesser number of effective control points.

In one embodiment, a desired dose, which includes an amount of radiation to be delivered to a treatment volume is received. A specification of an initial plurality of control points is also received. The radiation dose corresponding to the initial plurality of control points is calculated. The calculated dose and the desired dose are compared to determine the effect that each control point of the plurality of control points has on the comparison. A subset of the initial plurality of control points is selected, based on the comparison. The subset of the initial plurality of control points is consolidated into a lesser number of effective control points. The calculated dose corresponding to the subset of the control points and the calculated dose corresponding to the lesser number of effective control points are substantially the same.

Systems and computer readable medium for performing the above method are also disclosed.

BRIEF DESCRIPTION OF THE DRAWINGS

FIGS. 3(a-d) depict an exemplary iterative process of developing a treatment plan.

DETAILED DESCRIPTION OF THE INVENTION

Figure 1A:
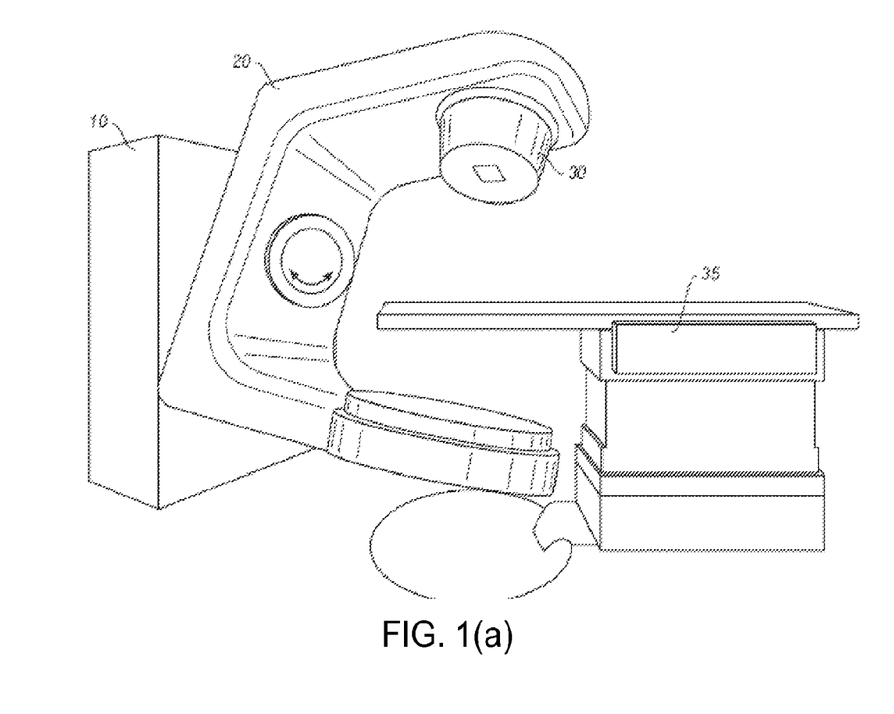
FIGS. 1(a) and 1(b) depict a radiation therapy system of the type which may be used in connection with an embodiment of the present invention.
Figure 1B:
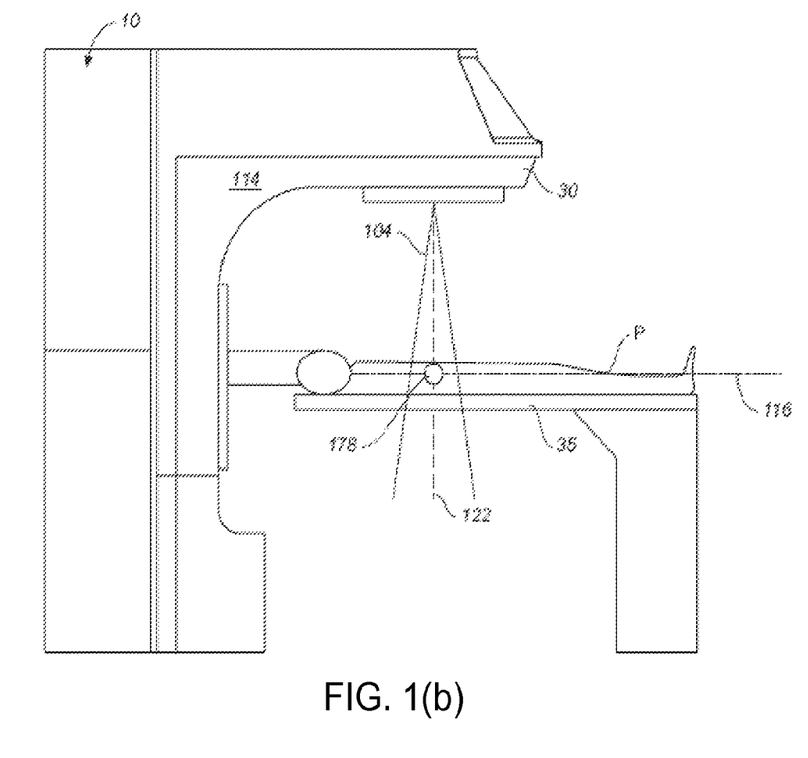

FIGS. 1(a) and 1(b) depict a radiation therapy system of the type which may be used in connection with the present invention. Referring to FIG. 1(a), a perspective view of radiation therapy system (in this case a linear accelerator) is shown. Typically, such a system is capable of generating either an electron (particle) beam or an x-ray (photon) beam for use in the radiotherapy treatment of patients on a treatment table 35. Other radiation therapy systems are capable of generating heavy particles such as protons. For purposes of the present discussion, only x-ray irradiation will be discussed. However, it will be appreciated by those skilled in the art that the same principles apply to other forms of irradiation.

Stand 10 supports a rotatable gantry 20 with a treatment head 30. A control unit (not shown) which includes operational electronics for controlling the system is coupled to stand 10. A high voltage source is provided within the stand or in the gantry, to supply voltage to an electron gun (not shown) positioned on an accelerator waveguide located in gantry 20. Electrons are emitted from the electron gun into the waveguide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 1(b), a somewhat more detailed side view of a radiation therapy system of the type which may be used in connection with the present invention is shown. A patient P is shown lying on treatment table 35. X-rays formed as described above are emitted from the target in treatment head 30 in a divergent beam 104. Typically, a patient plane 116, which is perpendicular to the page in FIG. 1(b), is positioned about one meter from the x-ray source or target, and the axis of gantry 20 is located on plane 116, such that the distance between the target and isocenter 178 remains constant when gantry 20 is rotated. Isocenter 178 is at the intersection between patient plane 116 and the central axis of beam 122. A treatment volume to be irradiated is located about the isocenter.

"Jaws" (not shown) or x-ray collimators comprising an x-ray blocking material, are positioned in head 30 to define the width of the x-ray beam at the patient plane. Typically, the jaws are moveable and, when fully open, define a maximum beam of about 40 cm×40 cm at patient plane 116. A multileaf collimator ("MLC") (not shown in FIG. 1(b)) is positioned at the exit of head 30, to further shape the x-ray beam. Since its introduction in 1990 the MLC has become a standard feature of most radiation therapy systems. MLCs currently sold by Varian Medical Systems, Inc., use up to 120 individually controllable leaves, typically thin slices of tungsten, that can be moved into or out of the x-ray beam under the control of system software. The MLC can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to the isocenter in the path of the x-ray beam, is defined by the jaws, the angle of the head and the MLC. In IMRT the leaves of the MLC are moved, such that the treatment volume comprises the total volume exposed during the course of a treatment. In arc therapy, the gantry is moved while radiation is delivered.

Figure 2:
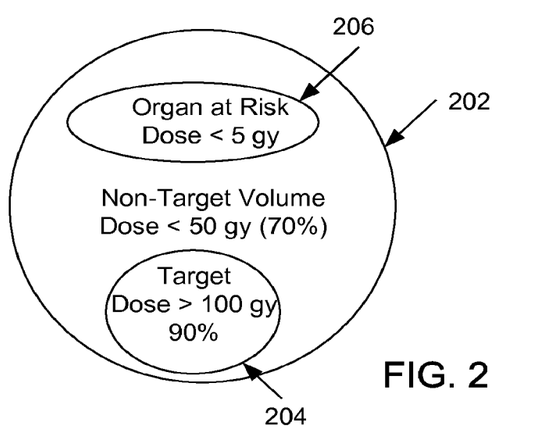
FIG. 2 depicts a cross section of a desired dose distribution for a treatment volume.

FIG. 2 depicts a cross section of a desired dose distribution for a treatment volume. As described in the background section, treatment planning typically begins with imaging of the treatment volume. FIG. 2 depicts a cross section of a treatment volume, such as may be obtained from a single slice of a CT image. As should be clear, the actual treatment volume is a three dimensional structure, however a cross section is depicted to simplify the description in order to more clearly understand embodiments of the present invention. This simplification is not intended to be limiting as the process as described is equally applicable to the actual three dimensional treatment volume. References to FIG. 2 and FIGS. 3(a-d) will be made in terms of a three dimensional structure, although the figures are presented as a two dimensional cross section.

Treatment volume 202 may be the volume of a patient that is to be irradiated. Treatment volume 202 may contain several structures that have been defined using the imaging techniques that have been discussed above. For example, treatment volume 202 may contain a target volume 204. Target volume 204 may be defined as a structure within treatment volume 202 that is to receive a therapeutic dose of radiation. For example, target volume 204 may be a tumor targeted for delivery of a prescribed dose of radiation.

Treatment volume 202 may also contain other structures, such as an organ at risk (OAR) 206. OAR 206 may be defined as a volume within treatment volume 202 that would be adversely affected by a dose of radiation in excess of a certain amount. The remainder of treatment volume 202 that is not a target volume 204 may not be as sensitive to radiation as OAR 206, but may also be constrained in the amount of radiation it can safely receive.

In order to develop a treatment plan, medical professionals, such as a radiation oncologist, may specify a desired radiation dose within the treatment volume 202. In some embodiments, the desired dose may be specified as a dose distribution within the treatment volume, although any other known methods of specifying a radiation dose would be suitable. For example, a clinician may determine that target volume 204 should receive a dose of at least 100 gy over 90% of the target volume. Likewise, the clinician may determine that OAR 206 may not receive more than 5 gy of radiation over the entire volume of OAR 206 in order to avoid any adverse results. Finally, the clinician may also determine that the remainder of the treatment volume 202 that is not the target volume 204 or an OAR 206 may receive up to a prescribed amount of radiation without causing an unacceptable level of adverse impact. The values for radiation doses in the following example are presented for the purpose of explanation only and are not intended to represent an actual treatment plan.

It should be clear that the above description is merely exemplary, and is in no way intended to be limiting. In alternate embodiments, a clinician may only specify dose values for each voxel within a treatment volume without specifying target volume 204 or OAR 206. In yet another embodiment, a clinician may define a desired dose volume histogram to establish the desired dose. In any case, once a prescribed dose has been defined, the process of developing a treatment plan for the delivery of the desired radiation dose may begin.

FIGS. 3(a-d) exemplify an iterative process of developing a treatment plan. Initially, a trajectory 302 of the radiation source about the treatment volume 304 is defined. For arc therapy, as depicted in FIG. 3(a), the trajectory may be an arc, typically a single 360° revolution, formed by the rotation of the treatment gantry (as depicted in FIG. 1) about the patient. Although this exemplary embodiment depicts an arc as the trajectory, it should be clear that this is only one possible trajectory. Any other trajectory as may be formed by movement along any of the motion axis as depicted in FIG. 1 would also be suitable. For example, a spiral trajectory may be created by rotating the gantry about the patient while simultaneously translating the treatment couch. Embodiments of the invention are suitable for any trajectory that may be formed by the motion of any or all of the motion axes as depicted in FIG. 1.

At the outset of the treatment planning process an initial number of control points 306(a-d) along trajectory 302 are specified. The initial number and position of the control points may be set in any convenient manner. For example the treatment planning software may use a set of initial control points by default or the initial control points may be specified by the system operator. Typically, the number of initial control points is small, but exceeds the four points shown in FIG. 3a. (Four is used in this example for purposes of simplification.)

Figure 3A:
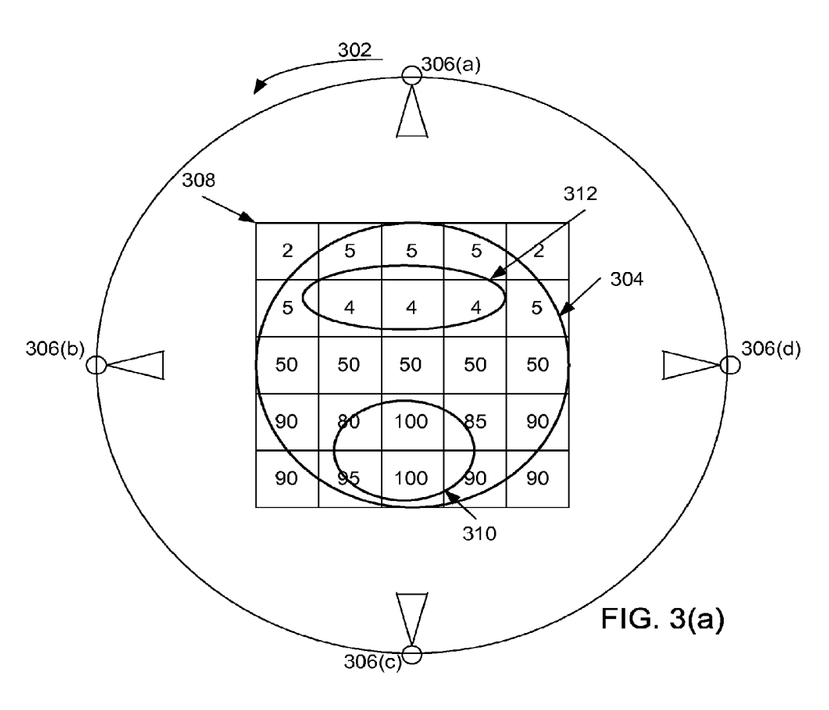

Each control point 306(a-d) is associated with a set of treatment parameters. For example, treatment parameters may include a set of MLC leaf positions, gantry rotation speed, intensity of the radiation source, or any other parameter. At the outset of treatment planning an initial set of treatment parameters is established for each of the initial control points. Again, the initial set of treatment parameters may be set by software default or by a system user. Techniques for establishing an initial set of control points and an initial set of treatment parameters for the control points are known and need not be discussed further.

Based on the treatment parameters, a dose distribution within the treatment volume is calculated for each control point by any number of techniques as have been discussed above. For example, the dose distribution within the treatment volume may be calculated based on pencil beam convolution, although any other suitable algorithm may also be used. FIG. 3(a) depicts an exemplary dose distribution grid 308 that has been superimposed on top of the treatment volume 304. The number within each box of the grid 308 represents the dose received by the corresponding voxel of the treatment volume from all of the control points 306(a-d) combined using the initial treatment parameters after a number of iterations of the treatment planning algorithm making adjustments as described below.

After each calculation of the dose distribution 308 within the treatment volume 304, a comparison can be made with the desired dose distribution as depicted in FIG. 2. If the dose distribution 308 does not conform to the desired dose distribution within a specified degree of accuracy, the process may continue using any number of search algorithms as discussed above to modify the treatment parameters. For example, the treatment parameters for each control point 306(a-d) may be slightly changed, and a new dose distribution calculation may be performed. If the resulting dose distribution 308 conforms to the desired dose distribution more closely than the previous set of treatment machine parameters, the new set of parameters may be selected. If the resulting dose distribution 308 is worse, the changes may be discarded, and the process performed again. The process of modifying treatment parameters for the specified control points 306(a-d) and recalculating the dose distribution may be iterated until a stopping point is reached. The stopping point may be defined by the search algorithm that is used, and may be based on various factors. For example, the process may be stopped after a predetermined number of iterations, a predetermined time period, or after achieving a predetermined level of correspondence between the desired dose distribution and the calculated dose distribution.

The complexity and, hence, difficulty of the calculation of the dose distribution 308 within the treatment volume is dependant on the number of control points 306(a-d) that are used. For each control point 306(a-d), the dose distribution within the treatment volume 304 must be calculated, and the resulting dose distributions from all the control points 306(a-d) must be aggregated. Thus, there is a trade-off when selecting the number of control points to use. Treatment planning typically begins with a smaller number of initial control points 306(a-d) to aid in arriving at an initial dose distribution, and additional control points are added as the process continues. Dose distribution 308 in FIG. 3(a) may depict the calculated dose distribution within the treatment volume using the initial set of control points 306(a-d) and iterating a defined number of times. As can be seen by comparing the calculated dose distribution 308 to the desired distribution in FIG. 2, the calculated dose distribution does not match the desired distribution. For example, the target volume 310 is prescribed to receive a dose greater than 100 gy over 90% of the target volume. Although the maximum dose received by OAR 312 is within the parameters as specified in FIG. 2, the treatment volume 304 is not within the specified parameters. The dose distribution as achieved with the initial set of control points 306(a-d) is unlikely to achieve the desired dose distribution. Dose distribution 308 may depict the calculated dose distribution as it may be after the stopping criteria for the initial set of control points 306(a-d) has been reached. Any number of stopping criteria, such as maximum iterations, maximum time, or a signal from an operator, may be used.

Figure 3B:
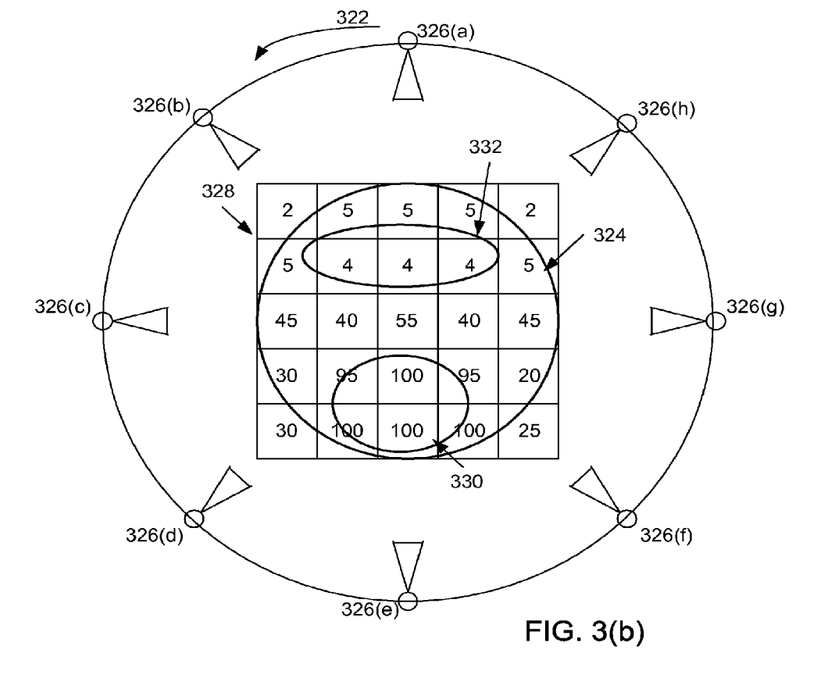

The treatment planning process then continues as depicted in FIG. 3(b). In FIG. 3(b) additional control points 326 are added to the defined trajectory 322. In some optimization algorithms, additional control points 326(b, d, f, h) are added between the existing control points 326(a, c, e, g). Treatment parameters for the new control points 326(b, d, f, h) may be selected in various ways. For example, they may be based on the treatment parameters of the adjacent control points 326(a, c, e, g). For example, if the leaves of the MLC are in a first position at control point 326a and are in a second position at control point 326c, the new control point 326b inserted between these two may initially use MLC leaf positions that are an average of the first and second positions. Once the new control points 326(a-h) have been added, the same process as presented with respect to FIG. 3(a) may be repeated.

For example, the dose distribution from each control point 326(a-h) of the expanded set of control points may be calculated using any of the well known techniques. The resulting dose distribution 328 may then be determined. The process of making changes to the new control points 326(a-h) can be iterated with the new set of control points until a desired stopping criteria is reached. As should be clear, the resulting larger number of control points 326(a-h) may result in a dose distribution 328 that conforms to the desired dose distribution more accurately. Dose distribution 328 depicts the calculated dose distribution as it may appear after the stopping criteria for the new number of control points 326(a-h) has been reached.

Figure 3C:
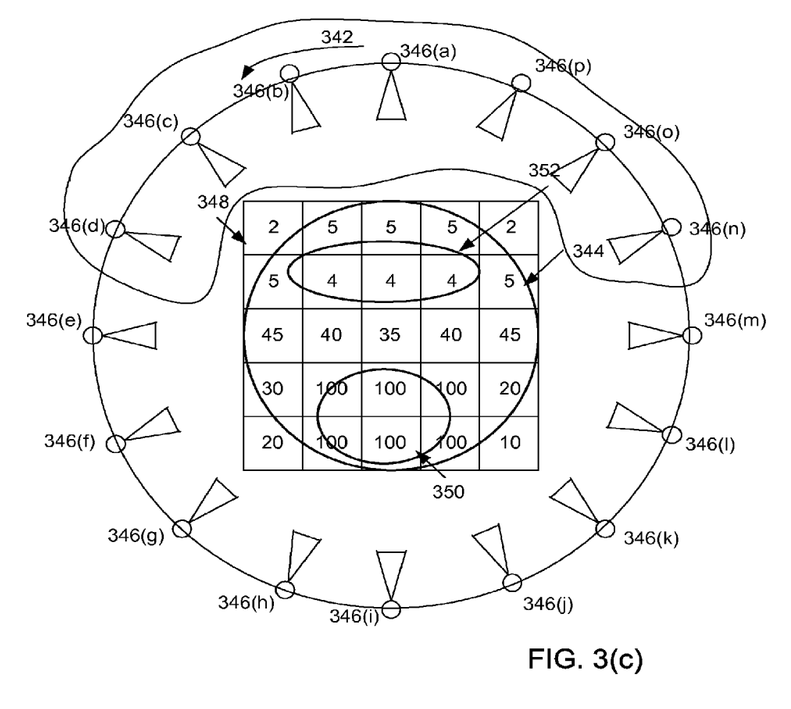

The process further continues as depicted in FIG. 3(c) by inserting even more control points 346(a-p). Generally using a larger number of control points facilitates the ability to achieve a treatment plan that closely matches the prescribed dose distribution, but once again the addition of more control points comes at a cost of increased computational load.

As the process continues, it may be determined that the dose delivered from certain control points along the trajectory does not significantly influence the dose distribution. For example, it may be determined after a few iterations that very little radiation should be delivered from a range of angles because of the presence of an OAR and, therefore, radiation from these angles does not contribute much to the calculated dose distribution. Thus, reviewing the first two rows of dose distribution 308, 328, 348 shows that dose distribution within those voxels does not change regardless of the number of control points. Reviewing FIGS. 3(a-c) it can be seen that the dose distribution for the bottom section of dose distribution 308, 328, 348 continues to more closely conform to the desired dose distribution as the number of control points are increased. As such, the addition of control points from treatment directions associated with the bottom portion of dose distribution 308, 328, 348 may be beneficial, whereas additional control points from treatment directions associated with the top portion of dose distribution 308, 328, 348 have limited or no effect.

The above example describes determining control points that are less important by examining the resultant calculated dose distribution after additional control points are added. However, this is only one possible way of determining less important control points. In other embodiments, less important control points may be determined by examining the calculated dose distribution from a fixed number of control points while the treatment parameters at those control points are varied. As explained above, treatment parameters may be optimized using a given number of control points using known search algorithms until a stopping point is reached. By examining the resultant dose distribution after each optimization cycle, less important control points can be determined. The less important control points can be determined for example, by selecting control points that have a lesser effect on the calculated dose distribution, regardless of the magnitude of the changes of the treatment parameters at those control points.

Although the above mentioned description has generically referenced calculating dose distributions from each control point using one of many known methods, it should be clear that this is not intended to imply that dose distribution calculation is a trivial process. In fact, the calculations using any of the known methods are time consuming and require significant amounts of computer processing power. Larger numbers of control points require ever increasing amounts of time and processing power to compute the dose distribution in the algorithms typically used in dose optimization. Because development of a treatment plan must occur within a finite time period, reducing the amount of time to calculate dose distribution would be advantageous. It may be advantageous because an acceptable treatment plan may be available for delivery to the patient at an earlier time. In the alternative, the time savings may be used to perform dose distribution calculations for additional control points that may be added for treatment directions that have the greatest impact on the desired dose distribution, leading to a treatment plan that more closely conforms to the desired dose distribution.

Embodiments of the present invention allow an improved method of treatment planning by consolidating control points that are less important in achieving a desired dose distribution into a smaller number of control points. This is contrary to the normal approach of continually adding control points. By reducing the number of control points significant reductions in time and required processing power are achieved because dose contribution from large numbers of less important control points can be modeled by a smaller number of control points. Furthermore, there may be no reduction in the number of control points from treatment directions which have a favorable impact on the desired dose distribution. The time savings achieved by reducing the number of less important control points may be used to add additional control points from treatment directions that are more important or to perform additional optimization of existing control points, leading to a better treatment plan in terms of user-given objectives.

Figure 3D:
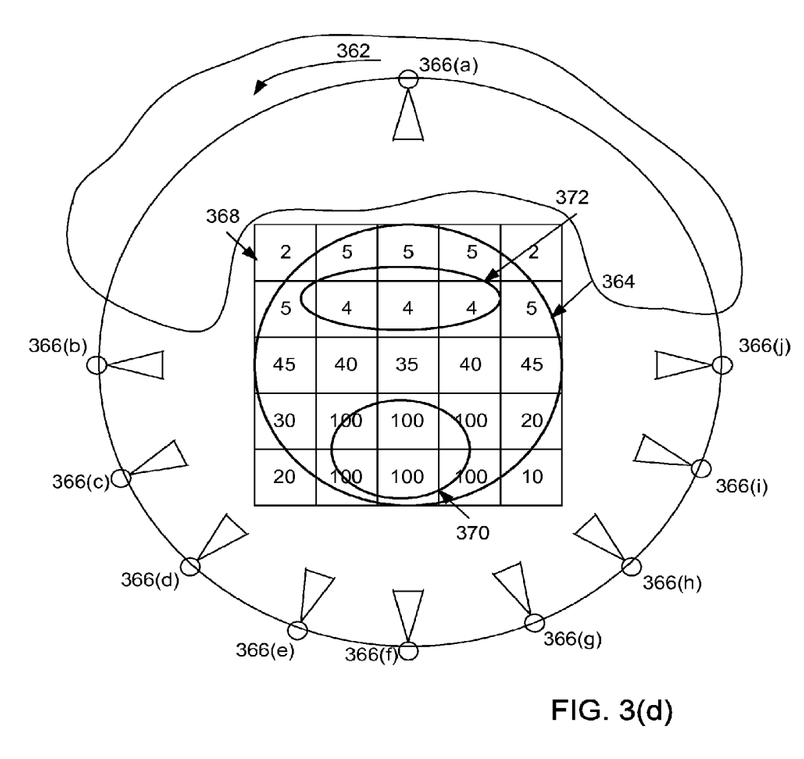

FIG. 3(d) depicts a new set of control points 366(a-j) as may exist after employing an embodiment of the present invention. As has been discussed with respect to FIGS. 3(a-c), control points around the upper section of treatment volume 364 have little effect on the desired dose distribution 368. However, each control point in that region still requires a full dose distribution calculation. As additional control points are added, additional calculations become necessary, with no corresponding increase in conformity of the treatment plan to the desired dose distribution. FIG. 3(d) depicts a single control point 366(a) that may be equivalent to seven less important control points 346(a-d, n-p) as depicted in FIG. 3(c). Although this example has shown seven control points 346 (a-d, n-p) being combined into a single control point 366(a), this is not limiting. Embodiments of the present invention may combine any number of less important control points into any smaller number of effective control points.

In order to consolidate a plurality of control points 346(a-d, n-p) into an effective control point 366(a), treatment machine parameters for the effective control point 366(a) may be determined. Embodiments of the present invention calculate treatment machine parameters for the effective control point 366(a) such that the dose distribution produced by the effective control point 366(a) may be substantially the same as the dose distribution produced by the plurality of control points 346(a-d, n-p). In one embodiment, machine parameters for the effective control point 366(a) are determined by calculating a weighted average of the machine parameters of all of the constituent control points 346(a-d, n-p). The weights of each of the constituent control points 346(a-d, n-p) may be different.

The preceding example has been presented in terms of direct optimization of machine parameters at each control point. In other embodiments of the invention, rather than calculating a dose distribution to the treatment volume based on machine parameters, a series of fluence maps from the control points may be optimized. The fluence from each control point may then be optimized similarly to optimization of machine parameters. Once a series of optimized fluence maps has been determined, machine parameters necessary at each control point to produce the desired fluence may be determined.

Consolidating fluences from a plurality of control points into an effective fluence from a lesser number of control points can occur similarly to machine parameter consolidation. For example, the fluence from each constituent control point 346(a-d, n-p) can be consolidated into a single effective fluence. A weighted average of the fluences from each constituent control point 346(a-d, n-p) may be calculated to determine an effective fluence from the effective control point 366(a). However, it should be noted that because fluence has a directional component, calculating the new fluence from an effective control point 366(a) may require more than the weighted average of the fluences from the constituent control points 346(a-d, n-p).

In one embodiment, the effective fluence is determined by projecting the fluences from each constituent control point 346(a-d, n-p) into an isocenter plane of the field of the effective control point, and summing the fluences. In this embodiment, the projection direction lies between the directions of the fields produced by the constituent control points 346(a-d, n-p) and the new effective control point 366(a). In another embodiment the average of the directions of the field of the effective control point 366(a) and the constituent control points 346(a-d, n-p) is used as the projection direction. By taking into account the fluences produced at each of the constituent control points 346(a-d, n-p), the fluence at the effective control point 366(a) may be corrected such that the dose distribution in the treatment volume remains substantially the same, regardless of if the dose is calculated from the constituent control points 346(a-d, n-p), or the effective control point 366(a).

The preceding exemplary embodiment of the invention has been presented in terms of control points as may exist with certain forms of radiation arc therapy. This simplified example was presented in order to provide an explanation of the invention in an embodiment that is easier to visualize in two dimensional space. It should be clear that the invention is not limited to arc therapy treatments, and is applicable to treatment planning for any number of additional forms of treatment. Control points may be specified based on any number of changing machine parameters, including, but not limited to, dose delivered, gantry angle, MLC settings, collimator angle, treatment couch position, treatment couch angle, or any combination thereof For example, in one embodiment, there may be no movement of the gantry around the patient at all, and the treatment parameter that is varied may be the intensity of the radiation dose. A control point may consist of the individual radiation dose intensities. In other embodiments, control points may be specified as the particular leaf positions of an MLC. Each control point could be a different set of MLC parameters. Furthermore, control points may be a combination of any variable machine parameters. For example, a control point may be defined as a combination of a radiation intensity, a gantry angle, an MLC angle, an MLC leaf position, and a treatment couch position. Any one of those parameters may be varied to define a new control point.

Embodiments of the invention determine control points that are less important to the overall dose delivered to the treatment volume, and consolidate those points into a lesser number of control points, thus reducing required dose calculations. The definition of the machine parameters that define a control point are not limited in any way. Rather, once control points are defined for any given type of therapy, embodiments of the invention may be used to more efficiently allocate dose computation resources to control points that are the most effective.

Furthermore, throughout the preceding example, the radiation dose to a treatment volume has been described in terms of a dose distribution. This simplification was in order to aid in understanding of the invention, and is not limiting. In some embodiments, instead of specifying a dose distribution for a treatment volume, the clinician may specify the desired dose using any other known methods of specifying a dose, such as a dose volume histogram. Embodiments of the invention are not limited by the particular scheme used to specify the desired dose, but rather are applicable to determine control points that are more important or less important to the desired dose. Embodiments of the invention are operable with any dose specification scheme.

Figure 4:
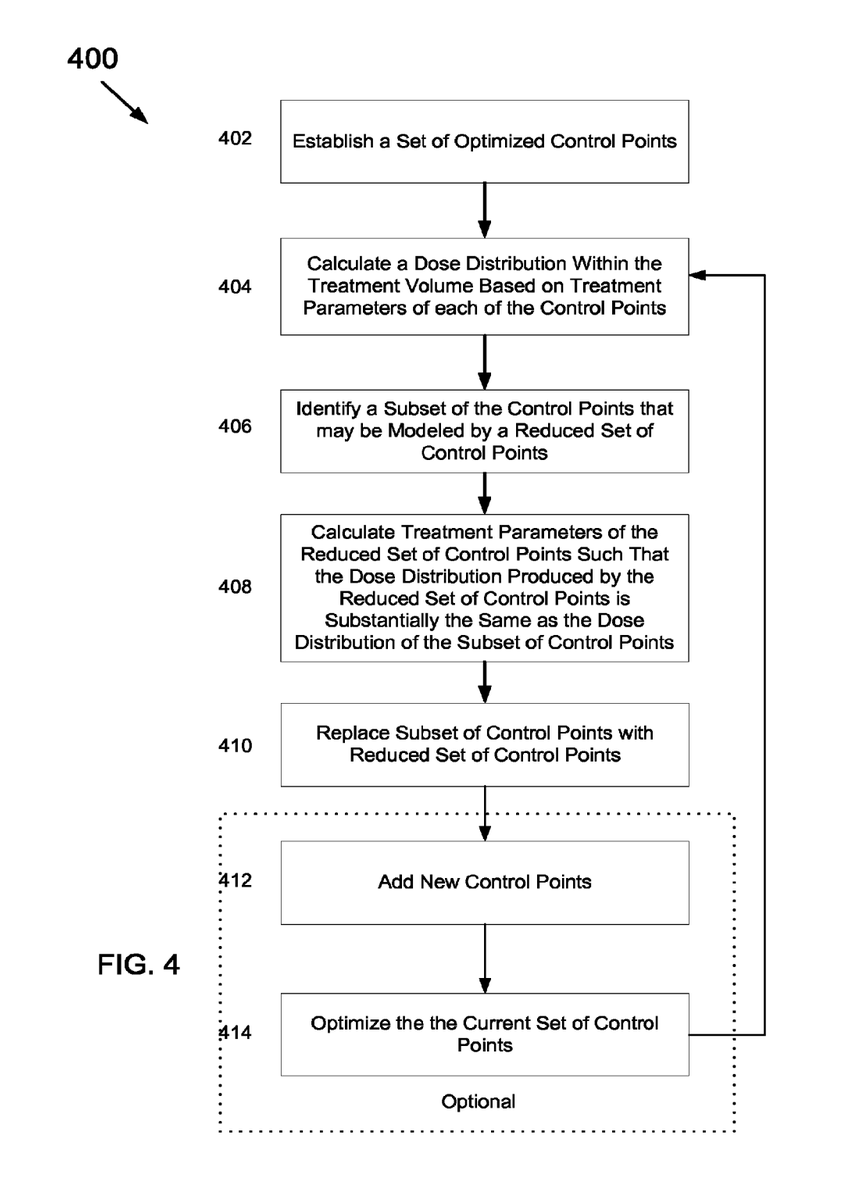
FIG. 4 depicts an exemplary method according to an embodiment of the invention.

FIG. 4 depicts an exemplary method according to an embodiment of the invention. Method 400 may begin at step 402 by establishing a set of optimized control points. As has been described above, a set of optimized control points is determined by starting with an initial set of control points and using various known search and dose calculation methods to obtain a set of treatment parameters for each of the control points.

At step 404, a dose distribution calculation is performed to obtain a dose distribution within the treatment volume based on the treatment parameters of each of the control points. Again, this step may be performed using any number of known dose distribution calculation methods. In some embodiments, step 404 is incorporated with step 402.

At step 406 a subset of the control points is identified as being appropriate for modeling by a reduced set of control points. As was described in relation to FIG. 3, control points that are determined to have a limited effect on the overall dose distribution may be selected as appropriate for modeling by a reduced set of control points.

At step 408, treatment parameters for the reduced set of control points are calculated. The treatment parameters for the reduced set of control points are calculated such that the dose distribution produced by the reduced set of control points is substantially the same as the dose distribution of the subset of control points. In other words, the machine parameters for the reduced set of control points are determined such that the dose delivered is substantially the same as the dose delivered by the larger set of control points.

At optional step 412, additional control points may be added. In some embodiments, additional control points may only be added at points along the treatment trajectory that have not already been modeled by a reduced set of control points. In other embodiments, additional control points may be added by doubling the current number of control points.

At optional step 414, the new set of control points is optimized. As discussed above, the optimization may be performed using any of a number of known techniques. The process then returns to step 404 and repeats for a number of iterations. The exact number of iterations may be determined by any suitable stopping criteria, such as sufficient conformation to desired dose distribution, a specific number of iterations performed, a certain time elapsing, or a signal from an operator. Once the stopping criteria have been reached, the treatment plan may be validated and delivered to a patient using an apparatus, such as the one depicted in FIG. 1.

Figure 5:
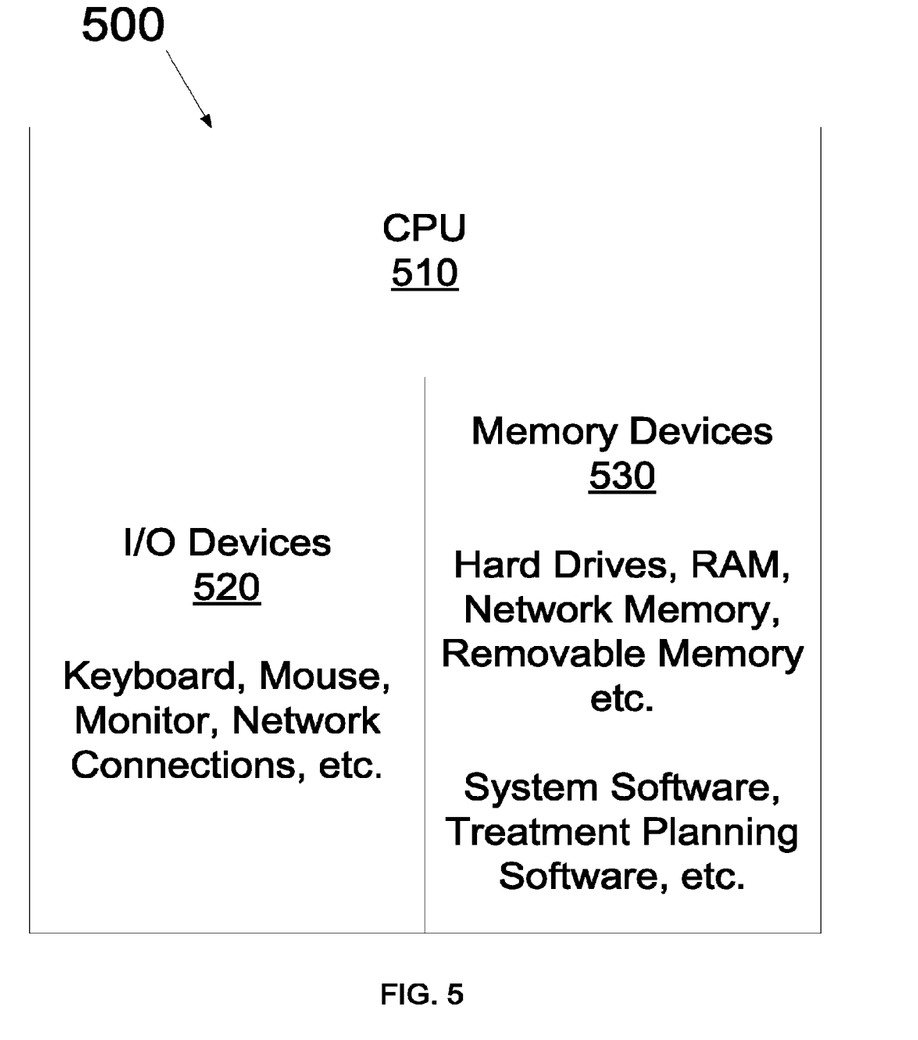
FIG. 5 represents a treatment planning system in accordance with an embodiment of the present invention.

FIG. 5 represents a treatment planning system 500 in accordance with the present invention. Treatment planning system 500 comprises a computer system having a central processing unit (CPU) 510 bidirectionally connected to various I/O devices 520, such as one or more keyboards, pointing devices, monitors, network connections, etc., and bidirectionally connected to various memory devices 530, such as one or more hard disks, random access memory, flash memory and/or remote memory devices accessed over a local or wide area computer network. While some memory devices are sometimes considered to be I/O devices, for convenience they are treated separately herein. Memory devices 530 comprise one or more tangible media for storing various system software programs. Collectively, CPU 510, I/O devices 520 and memory devices 530 constitute a computing system, which may additionally include other conventional elements typically found in computing systems.

According to the present invention, I/O devices 520 include one or more data input devices for entering patient data, for example, information about the tumor to be treated and about adjacent tissue structure, the prescribed dose to applied to the tumor, and the maximum radiation dose that can be tolerated by adjacent organs. Such patient data may comprise images from CT or MRI scans showing such structures. In one embodiment, I/O devices 520 comprise hardware and/or software tools to allow the system operator to digitize boundary and other information about such structures for use in treatment planning Software stored in memory devices 530 is loaded and processed in the computer system in any conventional manner. In accordance with the present invention, the software stored in memory devices 530 comprises software for optimizing a treatment plan for irradiating a target volume using a radiation therapy system having a multileaf collimator and capable of irradiating a treatment volume from a plurality of angles or while the gantry is in motion. The treatment planning software includes algorithms, such as algorithms for producing an effective control point from a set of constituent control points, necessary to implement the methods as described in FIG. 4. As indicated above in connection with FIG. 4, the software iteratively repeats machine parameter optimization until endpoint criteria are reached.

In a preferred embodiment the treatment planning system software further comprises an algorithm for translating the results of an optimized treatment plan into instructions for operating the radiation therapy system by controlling the positioning of the leaves of the multileaf collimator, the angle of irradiation, and dose rate. Treatment planning system can either be directly connected to system computer which controls the radiation system, the control instructions can be downloaded into the radiation system controller via a local or wide area network connection, or in any other known manner.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A computer implemented method of developing a treatment plan for the delivery of a desired dose of radiation to a treatment volume within a patient comprising:
receiving the desired dose, the desired dose indicating a desired amount of radiation to deliver to the treatment volume over time;
calculating a first dose to be delivered over a first delivery time using a first number of control points, wherein the calculated first dose is generally similar to the desired dose; and
calculating a second dose using a second number of control points that is less than the first number of control points, wherein the second dose is delivered over a second delivery time, and wherein the second delivery time is less than the first delivery time.

2. The method of claim 1 further comprising:
determining the effect that at least one of the first number of control points has on the calculated first dose; and
selecting the second number of control points based on the determined effect.

3. The method of claim 2 wherein the second number of control points are selected so as to exclude less important control points.

4. The method of claim 2 wherein selecting the second number of control points includes:
identifying a subset of the first number of control points; and
replacing the subset of the first number of control points with a reduced set of control points.

5. The method of claim 1 wherein the calculated second dose is generally similar to the desired dose.

6. A system for developing a treatment plan for the delivery of a desired dose of radiation to a treatment volume within a patient, the system comprising:
a processor; and
a memory coupled to the processor, the memory including instructions that when executed by the processor cause the processor to perform steps including:
receiving the desired dose, the desired dose indicating a desired amount of radiation to deliver to the treatment volume over time;
calculating a first dose to be delivered over a first delivery time using a first number of control points, wherein the calculated first dose is generally similar to the desired dose; and
calculating a second dose using a second number of control points that is less than the first number of control points,
wherein the second dose is delivered over a second delivery time, and wherein the second delivery time is less than the first amount of time.

7. The system of claim 6 wherein the first dose and the second dose are dose distributions.

8. The system of claim 7 wherein the dose distributions are defined in a three dimensional space.

9. The system of claim 6 wherein the memory includes instructions that when executed by the processor cause the processor to perform steps including:
- specifying an initial number of control points that is less than the first number of control points, and
- calculating an initial dose using the initial number of control points.

10. The system of claim 9 wherein the calculated initial dose does not match the desired dose.

11. A computer implemented method of developing a treatment plan for the delivery of a desired dose of radiation to a treatment volume within a patient comprising:
- receiving the desired dose, the desired dose indicating a desired amount of radiation to deliver to the treatment volume;
- calculating a first dose using a first number of control points, wherein the calculated first dose is generally similar to the desired dose; and
- calculating a second dose using a second number of control points that is less than the first number of control points, wherein the calculated second dose has substantially the same similarity to the desired dose.

12. The method of claim 11 wherein calculating a first dose includes optimizing at least one treatment parameter associated with each of the first number of control points.

13. The method of claim 11 wherein calculating a first dose includes optimizing at least one fluence map from the first number of control points.

14. The method of claim 11 further comprising:
- specifying an initial number of control points that is less than the first number of control points; and
- specifying the first number of control points based on the initial control points and a number of additional control points.

15. The method of claim 14 wherein the additional control points are provided at locations between the initial control points.

16. A system for developing a treatment plan for the delivery of a desired dose of radiation to a treatment volume within a patient, the system comprising:
- a processor; and
- a memory coupled to the processor, the memory including instructions that when executed by the processor cause the processor to perform steps including:
  - receiving the desired dose, the desired dose indicating a desired amount of radiation to deliver to the treatment volume;
  - calculating a first dose using a first number of control points, wherein the calculated first dose is generally similar to the desired dose; and
  - calculating a second dose using a second number of control points that is less than the first number of control points, wherein the calculated second dose has substantially the same similarity to the desired dose.

17. The system of claim 16 wherein the memory includes instructions that when executed by the processor cause the processor to perform steps including:
- identifying a subset of the first number of control points that may be modeled by a reduced set of control points such that the first number of control points includes the subset and remaining control points;
- calculating treatment parameters of the reduced set of control points such that the dose produced by the reduced set of control points is substantially the same as the dose of the subset of control points; and
- replacing the subset of the first number of control points with the reduced set of control points.

18. The system of claim 17 wherein the memory includes instructions that when executed by the processor cause the processor to perform steps including:
- specifying the second number of control points as the reduced set of control points and the remaining control points.

19. The system of claim 17 wherein the memory includes instructions that when executed by the processor cause the processor to perform steps including:
- adding new control points and specifying the second number of control points as the reduced set of control points, the remaining control points, and the new control points.

20. The system of claim 17 wherein at least some of the control points of the subset of the first number of control points do not significantly influence the calculated first dose.

* * * * *